(12) United States Patent
Wang et al.

(10) Patent No.: US 9,273,088 B2
(45) Date of Patent: Mar. 1, 2016

(54) GINSENOSIDE DERIVATIVE COMPOUNDS AND THE USE THEREOF IN PROTECTION AGAINST ISCHEMIA/REPERFUSION INJURY

(71) Applicant: Macau University of Science and Technology, Macau (CN)

(72) Inventors: Jingrong Wang, Macau (CN); Pei Luo, Macau (CN); Hua Zhou, Macau (CN); Wai In Chan, Macau (CN); Liang Liu, Macau (CN); Zhihong Jiang, Macau (CN)

(73) Assignee: Macau University of Science and Technology, Macau (CN)

( * ) Notice: Subject to any disclaimer, the term of this patent is extended or adjusted under 35 U.S.C. 154(b) by 110 days.

(21) Appl. No.: 14/055,883

(22) Filed: Oct. 17, 2013

(65) Prior Publication Data

US 2015/0112048 A1    Apr. 23, 2015

(51) Int. Cl.
*A61K 31/704* (2006.01)
*C07J 17/00* (2006.01)

(52) U.S. Cl.
CPC ............. *C07J 17/005* (2013.01); *A61K 31/704* (2013.01)

(58) Field of Classification Search
None
See application file for complete search history.

(56) References Cited

FOREIGN PATENT DOCUMENTS

CN          101880304    *    1/2010

OTHER PUBLICATIONS

Hobbs, A.; Foster, P.; Prescott, C.; Scotland, R.; Ahluwalia, A., Natriuretic peptide receptor-C regulates coronary blood flow and prevents myocardial ischemialreperfusion injury: novel cardioprotective role for endothelium-derived C-type natriuretic peptide. Circulation 2004, 110 (10), 1231-5.
Zhou, H.; Hou, S. Z.; Luo, P.; Zeng, B.; Wang, J. R.; Wong, Y. F.; Jiang, Z. H.; Liu, L., Ginseng protects rodent hearts from acute myocardial ischemia-reperfusion injury through GR/ER-activated RISK pathway in an endothelial NOS-dependent mechanism. J Ethnopharmacol 2011, 135 (2), 287-98.
Scott, G. I.; Colligan, P. B.; Ren, B. H.; Ren, J., Ginsenosides Rb1 and Re decrease cardiac contraction in adult rat ventricular myocytes: role of nitric oxide. Br J Pharmacol 2001, 134 (6), 1159-65.
Kang, S. Y.; Schini-Kerth, V. B.; Kim, N. D., Ginsenosides of the protopanaxatriol group cause endothelium-dependent relaxation in the rat aorta. Life Sci 1995, 56 (19), 1577-86.
Yi, X. Q.; Li, T.; Wang, J. R.; Wong, V. K.; Luo, P.; Wong, I. Y.; Jiang, Z. H.; Liu, L.; Zhou, H., Total ginsenosides increase coronary perfusion flow in isolated rat hearts through activation of PI3K/Akt-eNOS signaling. Phytomedicine 2010, 17 (13), 1006-15.
Wang, J. R.; Zhou, H.; Yi, X. Q.; Jiang, Z. H.; Liu, L., Total ginsenosides of Radix Ginseng modulates tricarboxylic acid cycle protein expression to enhance cardiac energy metabolism in ischemic rat heart tissues. Molecules 2012, 17 (11), 12746-57.
Jiang, Z.-H.; Fukuoka, R.; Aoki, F.; Tanaka, T.; Kouno, I., Dammarane-type triterpene glycosides from the leaves of *Rhoiptelea chiliantha*. Chem. Pharm. Bull. 1999, 47, 257-262.
Tu, Y.; Wang, Z.-X.; Shi, Y., An Efficient Asymmetric Epoxidation Method for trans-Olefins Mediated by a Fructose-Derived Ketone. J. Am. Chem. Soc. 1996, 118, 9806-9807.
Ko, S. R.; Suzuki, Y.; Kim, Y. H.; Choi, K. J., Enzymatic synthesis of two ginsenoside Re-beta-xylosides. Biosci Biotechnol Biochem 2001, 65 (5), 1223-6.
Ko, S. R.; Choi, K. J.; Suzuki, K.; Suzuki, Y., Enzymatic preparation of ginsenosides Rg2, Rh1, and F1. Chem Pharm Bull (Tokyo) 2003, 51 (4), 404-8.
Yoshikawa, M.; Murakami, T.; Ueno, T.; Hirokawa, N.; Yashiro, K.; Murakami, N.; Yamahara, J.; Matsuda, H.; Saijoh, R.; Tanaka, O., Bioactive saponins and glycosides. IX. Notoginseng (2): structures of five new dammarane-type triterpene oligoglycosides, notoginsenosides-E, -G, -H, -I, and -J, and a novel acetylenic fatty acid glycoside, notoginsenic acid β-sophoroside, from the dried root of *Panax notoginseng* (Burk.) F. H. Chen. Chem. Pharm. Bull. 1997, 45 (Copyright (C) 2012 American Chemical Society (ACS). All Rights Reserved.), 1056-1062.
Kasai, R.; Hara, K; Dokan, R.; Suzuki, N.; Mizutare, T.; Yoshihara, S.; Yamasaki, K., Major metabolites of ginseng sapogenins formed by rat liver microsomes. Chem Pharm Bull (Tokyo) 2000, 48 (8), 1226-7.
Odani, T.; Tanizawa, H.; Takino, Y., Studies on the absorption, distribution, excretion and metabolism of ginseng saponins. IV. Decomposition of ginsenoside-Rg1 and -Rb1 in the digestive tract of rats. Chem Pharm Bull (Tokyo) 1983, 31 (10), 3691-7.
Duc, N. M.; Kasai, R.; Ohtani, K.; Ito, A.; Nham, N. T.; Yamasaki, K.; Tanaka, O., Saponins from Vietnamese ginseng, Panax-vietnamensis Ha-et-Grushv. collected in central Vietnam. III. Chem Pharm Bull (Tokyo) 1994, 42 (3), 634-40.
Yoshikawa, M.; Murakami, T.; Ueno, T.; Yashiro, K.; Hirokawa, N.; Murakami, N.; Yamahara, J.; Matsuda, H.; Saijoh, R.; Tanaka, O., Bioactive saponins and glycosides. VIII. Notoginseng (1): new dammarane-type triterpene oligoglycosides, notoginsenosides-A, -B, -C, and -D, from the dried root of *Panax notoginseng* (Burk.) F.H. Chen. Chem Pharm Bull (Tokyo) 1997, 45 (6), 1039-45.
Nguyen, M. D.; Kasai, R.; Ohtani, K.; Ito, A.; Nguyen, T. N.; Yamasaki, K.; Tanaka, O., Saponins from Vietnamese Ginseng, *Panax vietnamensis* HA et Grushv. Collected in central Vietnam. II. Chem Pharm Bull (Tokyo) 1994, 42 (1), 115-22.

* cited by examiner

*Primary Examiner* — Traviss C McIntosh, III
(74) *Attorney, Agent, or Firm* — Eagle IP Limited; Jacqueline C. Lui (57) ABSTRACT

The present invention provides novel ginsenoside derivative compounds and the use thereof in protection against ischemia/reperfusion injury.

2 Claims, 4 Drawing Sheets

GINSENOSIDE DERIVATIVE COMPOUNDS AND THE USE THEREOF IN PROTECTION AGAINST ISCHEMIA/REPERFUSION INJURY

FIELD OF INVENTION

This invention relates to novel ginsenoside derivative compounds and the use thereof in protection against ischemia/reperfusion injury.

BACKGROUND OF INVENTION

Ischemic heart diseases are one of the leading causes of death in humans in the industrialized countries. Although ischemic injury of heart tissues can be greatly recovered by rapid reperfusion, severe side effects such as cardiac over-contractile function, arrhythmia, endothelial dysfunction, and myocardial infarction often occur due to reperfusion. Moreover, endothelial dysfunction in ischemic heart tissues may lead to the loss of the endothelium-derived dilator of nitric oxide (NO), decrease of blood perfusion in the tissues, myocytes apoptosis, non-infectious inflammation and other complicated cardiac pathological status [1]. Therefore, ischemia/reperfusion (I/R) injury has been evidenced as one of the most pivotal pathological factors of human ischemic heart diseases.

Ginsenosides have been demonstrated as the major chemical components of ginseng herb responsible for the most observed bioactivities in clinical usage. In vivo and in vitro investigations have revealed a number of significant effects of ginsenosides and ginseng extracts in cardio-protection, such as reducing myocardial ischemia-reperfusion induced damage via NO pathway in rats and mice [2], slowing down deterioration of cardiac contractions, preventing development of arrhythmias [3] and relaxing the muscles of the aorta [4]. Previous studies by the inventors of the present invention showed that total ginsenosides (TGS) significantly increased coronary artery flow in both basal perfusion and I/R injury condition of the isolated rat hearts in Langendorff system through activating Akt-eNOS signaling, which suggests that TGS could benefit patients with ischemic heart conditions [5]. The inventors further discovered the molecular mechanisms underlying the myocardial protection of TGS through proteomic analysis with two-dimensional gel electrophoresis (2-DE) and MALDI-TOF-TOF-MS techniques, revealing that improvement of cardiac energy metabolism via activating proteins in tricarboxylic acid cycle (TCA cycle) could be the major action pathway and targets of TGS activity against rat heart tissue injury [6].

As mentioned, ginsenosides may be a potential source to isolate effective compounds for protection against I/R injury.

SUMMARY OF INVENTION

In the light of the foregoing background, it is an object of the present invention to provide novel ginsenoside derivative compounds and novel uses thereof in protection against I/R injury.

Accordingly, the present invention, in one aspect, provides a ginsenoside derivative compound, which is represented by formula (I) or any optical isomer thereof, (I)

in which R1 is represented by Glc-$^2$Glc-O—; R3 is a group represented by formula (II), (III), or (IV), or an epimer thereof. In the formulas (II) and (III), R2 is a group represented by —H.

(II)

(III)

(IV)

In an exemplary embodiment of the present invention, R3 is represented by formula (II) and comprises stereocenters at C-20 and C-24, the stereocenter being either 'R' or 'S' in configuration.

In a further exemplary embodiment of the present invention, the stereocenter at C-20 is 'S' in configuration; the compound is 3-O-[β-D-glucopyranosyl(1→2)-β-D-glucopyranosyl]-3β,12β,20(S),24(S)-tetrahydroxydammar-25-ene and 24(R) epimer thereof, and presented by formula (V).

(V)

In another further exemplary embodiment of the present invention, the stereocenter at C-20 is 'R' in configuration; the compound is 3-O-[β-D-glucopyranosyl(1→2)-β-D-glucopyranosyl]-3β,12β,20(R),24(S)-tetrahydroxydammar-25-ene and 24(R) epimer thereof, and presented by formula (V).

In another exemplary embodiment of the present invention, R3 is represented by formula (III) and comprises a stereocenter at C-20, the stereocenter being either 'R' or 'S' in configuration.

In a further exemplary embodiment of the present invention, the stereocenter is 'S' in configuration; the compound is 3-O-[β-D-glucopyranosyl(1→2)-β-D-glucopyranosyl]-3β,12β,20(S),25-tetra-hydroxydammar-23-ene and presented by formula (VI).

(VI)

In another further exemplary embodiment of the present invention, the stereocenter is 'R' in configuration; the compound is 3-O-[β-D-glucopyranosyl(1→2)β-D-glucopyranosyl]-3β,12β,20(R),25-tetra-hydroxydammar-23-ene and presented by formula (VI).

In another exemplary embodiment of the present invention, R3 is represented by formula (IV) and comprises stereocenter at C-20, said stereocenter being 'R' in configuration; said compound is 3-O-[β-D-glucopyranosyl(1→2)-β-D-glucopyranosyl]-20(R),24(S)-epoxydammarane-3β,12β-triol and 24(R) epimer thereof, and presented by formula (VII).

(VII)

The present invention, in another aspect, provides a method of synthesizing ginsenoside derivative compounds comprising steps of:
a) providing a ginsenoside starting material;
b) mixing the ginsenoside starting material with a stain;
c) photosensitizing the mixture;
d) filtrating the photosensitized mixture
e) adding organophosphorus compound to said filtrate;
f) drying the solution of step (e); and
g) subjecting the solution of step (f) to combinative column chromatography to obtain said ginsenoside derivative compounds.

In an exemplary embodiment of the present invention, the step (c) further comprises irradiating the mixture with 400 W lamp under an oxygen atmosphere at room temperature for 10 h; in the step (e) the organophosphorus compound is triphenylphosphine; the step (e) further comprises stirring the filtrate at room temperature for 4 h; the step (f) further comprises evaporating the solution to dryness of step (e) in vacuum; and the step (g) further comprises subjecting the solution of step (f) to combinative column chromatography over silica gel eluted with $CHCl_3$-MeOH, MCI-gel CHP 20P, and Bondpack ODS eluted with 40~100% MeOH.

In another exemplary embodiment of the present invention, the ginsenoside starting material is 20(S)-$Rg_3$ and/or 20(R)-$Rg_3$. In a further exemplary embodiment of the present invention, the ginsenoside derivative compound is represented by formula (I) or any optical isomer thereof; said $R_3$ is a group represented by formula (II) or (III), or an epimer thereof.

The present invention, in a further aspect, provides a method of synthesizing ginsenoside derivative compounds comprising steps of:
a) providing a ginsenoside starting material in solution;
b) adding an epoxidation dibetal catalyst solution and the mixture of sodium bicarbonate and oxone to said ginsenoside starting material solution;
c) stirring the solution of step (b);
d) extracting the solution of step (c) with n-BuOH to obtain resultant n-BuOH layer; and
e) subjecting the resultant n-BuOH layer to combinative column chromatography to obtain said ginsenoside derivative compounds.

In an exemplary embodiment of the present invention, the ginsenoside starting material is provided in acetonitrile solution; the step (a) further comprises mixing the ginsenoside starting material with an aqueous EDTA-Na solution and cooling the mixed solution to 0° C.; the epoxidation dibetal catalyst solution is ketone in acetonitrile; in the step (c), the solution of step (b) is stirred overnight at 0° C.; the step (e) further comprises subjecting the resultant n-BuOH layer to column chromatography over $SiO_2$ and ODS eluted with $CHCl_3$-MeOH, MCI-gel CHP 20P, and Bondpack ODS eluted with 30-100% MeOH.

In another exemplary embodiment of the present invention, the ginsenoside starting material is 20(S)-$Rg_3$. In a further exemplary embodiment of the present invention, the ginsenoside derivative compound is represented by formula (I) or any optical isomer thereof; the R3 is a group represented by formula (IV).

The present invention, in another aspect, provides a method of preventing ischemia/reperfusion injury in cardiomyocytes comprises administering an effective amount of said ginsenoside derivative compound of one aspect of present invention to a subject in need thereof.

In an exemplary embodiment of the present invention, the ginsenoside derivative compound is selected from the group consisting of 3-O-[β-D-glucopyranosyl(1→2)-β-D-glucopyranosyl]-3β,12β,20(S),24(S)-tetrahydroxydammar-25-ene and 24(R) epimer thereof; 3-O-[β-D-glucopyranosyl(1→2)-β-D-glucopyranosyl]-3β,12β,20(S),25-tetra-hydroxydammar-23-ene; 3-O-[β-D-glucopyranosyl(1→2)-β-D-glucopyranosyl]-3β,12β,20(R),24(S)-tetrahydroxydammar-25-ene and 24(R) epimer thereof; 3-O-[β-D-glucopyranosyl(1→2)-β-D-glucopyranosyl]-3β,12β,20(R),25-tetrahydroxydammar-23-ene; and 3-O-[β-D-glucopyranosyl(1→2)-β-D-glucopyranosyl]-20(R),24(S)-epoxydammarane-3β,12β-triol and 24(R) epimer thereof.

The present invention, in another aspect, provides a method of treating ischemia/reperfusion injury in cardiomyocytes comprises administering an effective amount of said ginsenoside derivative of one aspect of present invention to a subject in need thereof.

In an exemplary embodiment of the present invention, the synthesized ginsenoside derivative is selected from a group consisting of 3-O-[β-D-glucopyranosyl(1→2)-β-D-glucopyranosyl]-3β,12β,20(S),24 (S)-tetrahydroxydammar-25-ene and 24(R) epimer thereof; 3-O-[β-D-glucopyranosyl(1→2)-β-D-glucopyranosyl]-3β,12β,20(S),25-tetra-hydroxydammar-23-ene; 3-O-[β-D-glucopyranosyl(1→2)-β-D-glucopyranosyl]-3β,12β,20(R),24(S)-tetrahydroxydammar-25-ene and 24(R) epimer thereof; 3-O-[β-D-glucopyranosyl(1→2)-β-D-glucopyranosyl]-3β,12β,20(R),25-tetrahydroxydammar-23-ene; and 3-O-[β-D-glucopyranosyl(1→2)-β-D-glucopyranosyl]-20(R),24(S)-epoxydammarane-3β,12β-triol and 24(R) epimer thereof.

DETAILED DESCRIPTION OF THE PREFERRED EMBODIMENTS

As used herein and in the claims, "comprising" means including the following elements but not excluding others.

The below examples demonstrate new synthesized ginsenoside derivative compounds of the present invention and the use thereof in protection against ischemia/reperfusion injury in cardiomyocytes.

EXAMPLE 1

This example describes the methodologies for the organic synthesis of ginsenoside derivatives, compounds A-G, from natural ginsenosides $Rg_3$ and $Rh_2$.

1. Chemical Synthesis of Compounds A-G

The compounds A-G and the staring materials thereof are shown in Table 1

TABLE 1

Compounds A-G and the staring materials thereof

| Compound | Ginsenoside Starting Material |
|---|---|
| A | 20 (S)-$Rg_3$ |
| B | 20 (S)-$Rg_3$ |
| C | 20 (R)-$Rg_3$ |
| D | 20 (R)-$Rg_3$ |

TABLE 1-continued

Compounds A-G and the staring materials thereof

| Compound | Ginsenoside Starting Material |
|---|---|
| E | 20 (R)-$Rg_3$ |
| F | 20 (S)-$Rg_3$ |
| G | 20 (S)-$Rh_2$ |

Figure 1A:
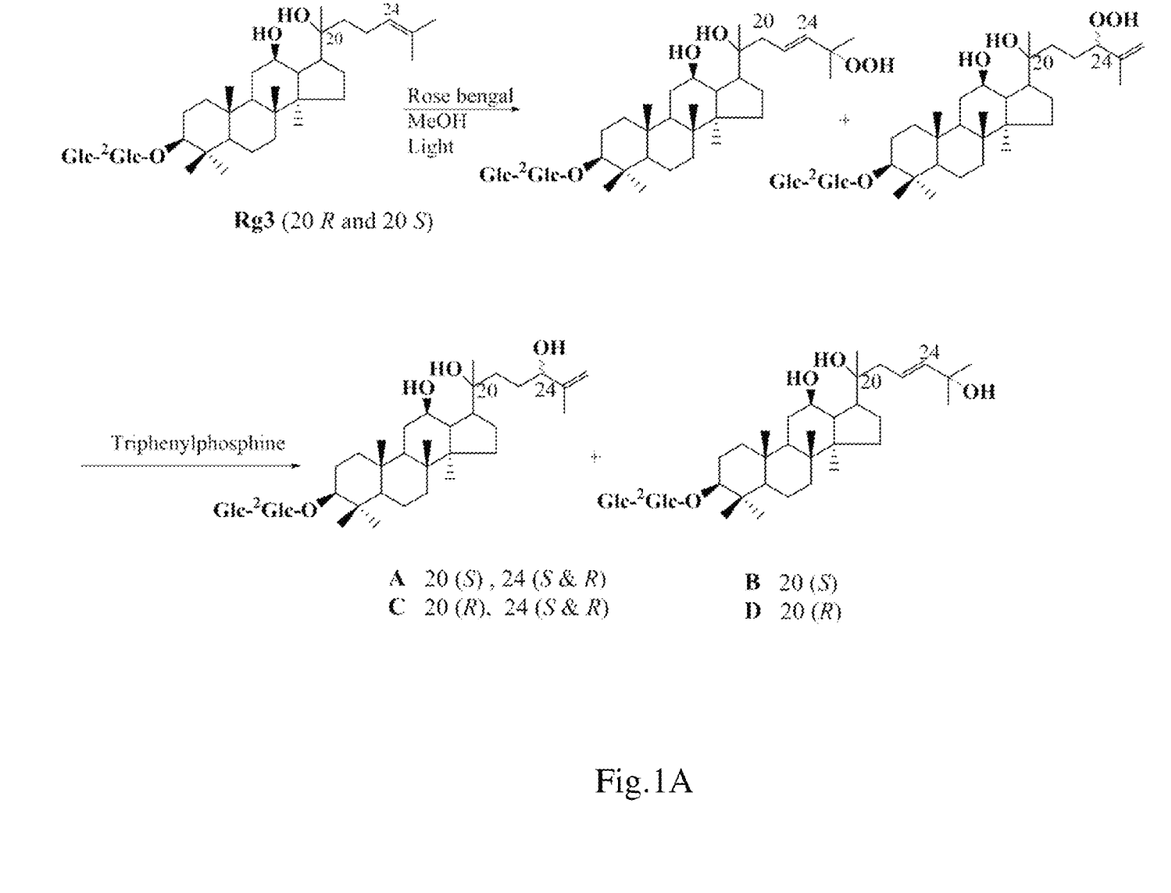
FIG. 1A shows the chemical synthesis and chemical structure of gensenoside derivative compounds A-D.

The synthesis of compounds A-D, new derivative compounds of the natural ginsenosides 20(S)-$Rg_3$ and 20(R)-$Rg_3$ is carried out according to the protocol described by Jiang et. al. [7]. Briefly, a solution of the ginsenoside starting material of 20(S)-$Rg_3$ or 20(R)-$Rg_3$ (200 mg) and Rose-Bengal (20 mg) in 150 ml MeOH is stirred and irradiated with 400 W lamp under an oxygen atmosphere at room temperature for 10 h. After filtration, triphenylphosphine (40 mg) is added to the filtrate and the solution is stirred again at room temperature for another 4 h and then evaporated to dry a concentrated solution to 1-5 ml in vacuum. Afterwards, the concentrated solution is subjected to combinative column chromatography over silica gel eluted with $CHCl_3$-MeOH (gradient from 10:0 to 8:2 volume ratio), then over MCI-gel CHP 20P and Bondpack ODS eluted with 40~100% MeOH. The eluent containing target compounds were combined and dried to obtain individual the oxygenated products. Finally, 30.3 mg of compound A, 35.0 mg of compound B, 38.2 mg of compound C and 39.2 mg of compound D are synthesized, with the respective structures as shown in FIG. 1A.

Figure 1B:
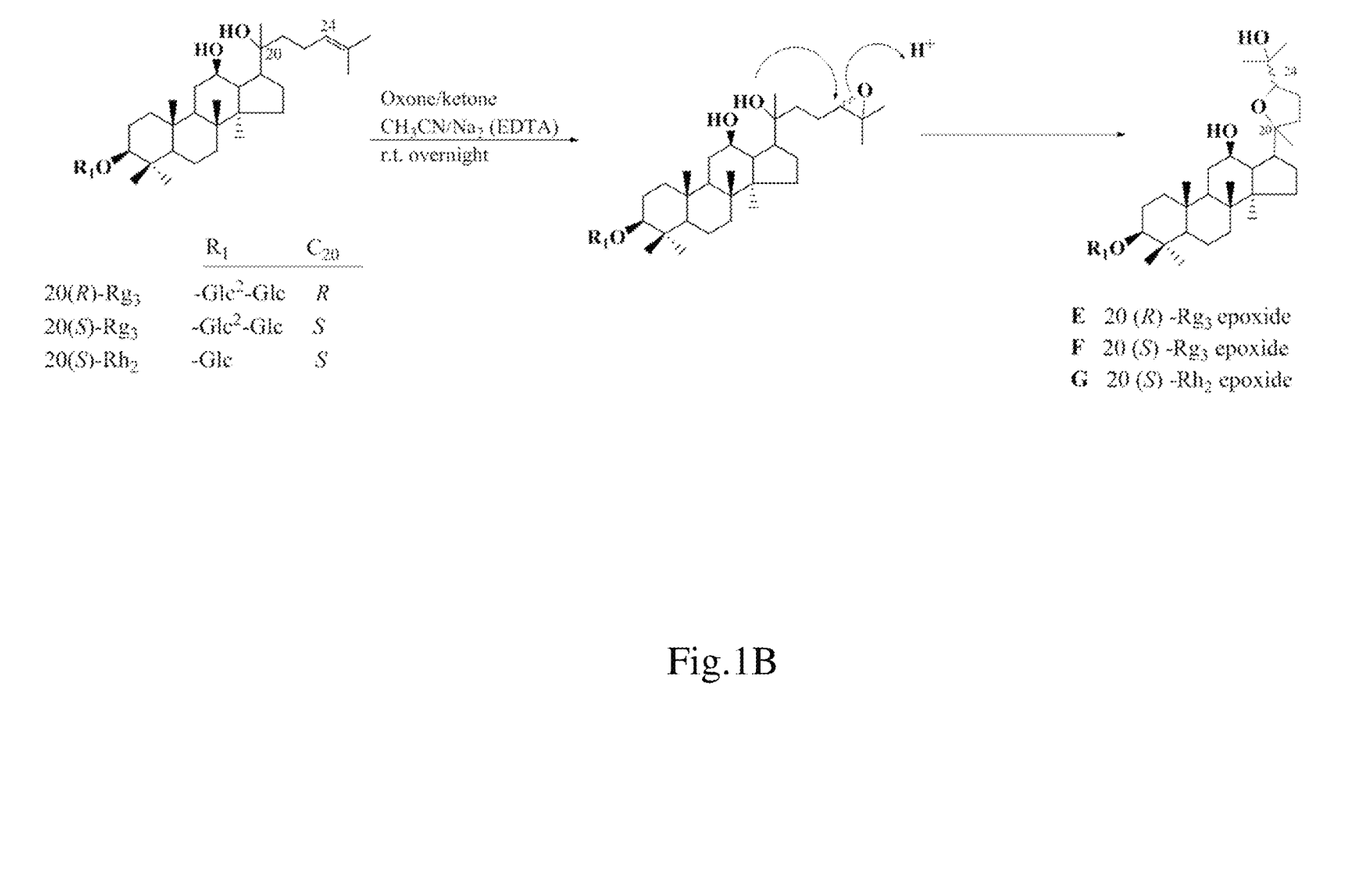
FIG. 1B shows the chemical synthesis and chemical structure of gensenoside derivative compounds E-G.

The process of the chemical synthesis of compounds E-G, new derivative compounds of the natural ginsenosides 20(S)-$Rg_3$, 20(R)-$Rg_3$, and 20 (S)-$Rh_2$, is performed following the procedure described by Tu et. al. [8] with minor modifications. Briefly, solution of the starting ginsenoside material (100 mg) in acetonitrile (10 ml) is mixed with an aqueous EDTA-Na solution (0.4 μM, 10 ml). The mixed solution is cooled to 0° C. and then an epoxidation dibetal catalyst solution (ketone, 60 μM in acetonitrile, 1-5 ml) and the 1-2 ml mixture of sodium bicarbonate (155 μM) and oxone (100 μM) are added. The homogenous solution is stirred overnight at room temperature and then extracted with n-BuOH. The resultant n-BuOH layer is applied to column chromatography over $SiO_2$ and ODS. The eluent containing target compounds were combined and dried to obtain 21.6 mg of compound E, 15.02 mg of compound F, and 18.0 mg of compound G, with the respective structures as shown in FIG. 1B.

2. Identification of Compounds A-E

Among the derivative compounds synthesized from the aforesaid processes, compounds A to E are new ginsenosides in which the chemical structures thereof are characterized based on $^1$H-and $^{13}$C-NMR data. Compounds F and G are identified based on high-resolution MS obtained on Q-TOF-MS. In the following paragraphs, identification of each of compounds A-E is described.

Compound A: 3-O-[β-D-glucopyranosyl(1→2)-β-D-glucopyranosyl]-3β,12β,20(S), 24(S)-tetrahydroxydammar-25-ene and its 24(R) epimer; white powder; $^1$H-NMR (pyridine-$d_5$, 300 MHz) δ: 0.80, 0.95, 0.98, 1.10, 1.29, 1.46 (3H each, all s), 1.89, 1.93 (1.5H each, s, H-27 of 24(S) and 24(R)), 3.30 (1H, dd, J=11.4, 3.9 Hz, H-3), 3.92 (1H, m, H-12), 4.44 (1H, dd, J=12.0, 4.2 Hz, H-24), 4.91 (1H, d, J=7.5 Hz, H-1'), 4.93 (1H, s, H-26), 5.25 (1H, s, H-26), 5.37 (1H, d, J=7.5 Hz, H-1"); $^{13}$C-NMR data was shown in Table 2.

Compound B: 3-O-[β-D-glucopyranosyl(1→2)-β-D-glucopyranosyl]-3β,12β,20(S),25-tetra-hydroxydammar-23- ene; white powder; $^1$H-NMR (pyridine-d$_5$, 300 MHz) δ: 0.85, 0.97, 1.06, 1.13, 1.31, 1.45, 1.56, 1.57 (3H each, all s, CH$_3$-30, 19, 18, 29, 28, 26, 27), 3.30 (1H, dd, J=11.4, 4.2 Hz, H-3), 3.93 (1H, m, H-12), 4.93 (1H, d, J=7.2 Hz, H-1'), 5.39 (1H, d, J=7.5 Hz, H-1"), 6.03 (1H, d, J=15.6 Hz, H-24), 6.31 (1H, ddd, J=15.0, 8.4, 5.4 Hz, H-23); $^{13}$C-NMR data was shown in Table 2.

Compound C: 3-O-[β-D-glucopyranosyl(1→2)-β-D-glucopyranosyl]-3β,12β,20(R), 24(S)-tetrahydroxydammar-25-ene and its 24(R) epimer; white powder; $^1$H-NMR (pyridine-d$_5$, 300 MHz) δ: 0.83, 0.97, 1.02, 1.14, 1.32, 1.44 (3H each, all s, CH$_3$-30, 19, 18, 29, 26, 28), 1.95, 1.97 (1.5H each, s, CH$_3$-27 of 24(S) and 24(R)), 3.30 (1H, dd, J=11.4, 3.9 Hz, H-3), 3.98 (1H, m, H-12), 4.31 (1H, dd, J=12.6, 4.5 Hz, H-24), 4.97 (1H, d, J=7.8 Hz, H-1'), 4.98 (1H, s, H$_b$-26), 5.33 (1H, s, H$_a$-26), 5.42 (1H, d, J=7.8 Hz, H-1"); $^{13}$C-NMR data was shown in Table 2.

Compound D: 3-O-[β-D-glucopyranosyl(1→2)-β-D-glucopyranosyl]-3β,12β,20(R), 25-tetrahydroxydammar-23-ene; white powder; $^1$H-NMR (pyridine-d$_5$, 300 MHz) δ: 0.82, 0.95, 1.02, 1.11, 1.29, 1.42 (3H each, all s), 1.56 (6H, s, CH$_3$-26, 27), 3.26 (1H, dd, J=11.7, 4.5 Hz, H-3), 3.93 (1H, m, H-12), 4.92 (1H, d, J=7.2 Hz, H-1'), 5.39 (1H, d, J=7.5 Hz, H-1"), 6.03 (1H, d, J=16.4 Hz, H-24), 6.50 (1H, ddd, J=15.0, 7.2, 5.4 Hz, H-23); $^{13}$C-NMR data was shown in Table 2.

Compound E: 3-O-[β-D-glucopyranosyl(1→2)-β-D-glucopyranosyl]-20(R), 24(S)-epoxydammarane-3β,12β-triol and its 24(R) epimer; white powder; $^1$H-NMR (pyridine-d$_5$, 400 MHz) δ: 0.79, 1.01, 1.22, 1.29, 1.33, 1.45, 1.46, 2.04 (3H each, s), 3.51 (1H, dd, J=11.0, 5.0 Hz, H-3), 3.74 (1H, m, H-12), 4.09 (1H, dd, J=9.7, 3.8 Hz, H-24), 4.94 (1H, d, J=7.2 Hz, H-1'), 5.40 (1H, d, J=7.5 Hz, H-1"); $^{13}$C-NMR data was shown in Table 2.

3. Results

Compounds A-D were synthesized through photosensitized oxygenation. Chemical structures of the synthesized compounds were confirmed based on spectroscopic studies. In one embodiment of the instant invention, compound B was synthesized using 20(S)-Rg$_3$ as the ginsenoside starting material, showing the structure elucidation of photosensitized ginsenosides. The proton and carbon signals of aglycone part in the $^1$H-NMR and $^{13}$C-NMR spectrum of compound B were found to be very similar to that of 20(S)-Rg$_3$ in literature except for some signals arising from the side chain [9]. A disubstituted olefin as evidenced by the signals at δ$_H$ 6.03 (1H, d, J=15.6 Hz, H-24), 6.31 (1H, ddd, J=15.0, 8.4, 5.4 Hz, H-23) and δ$_C$ 123.3 (C-23), 141.8 (C-24), and the downfield shift of C-22 (Δδ$_C$=3.5 ppm) comparing to that of 20(S)-Rg$_3$, clearly indicated that a translocation of the double bonds to C-23 and C-24. The oxygenated carbon (δ$_C$ 69.9) assigned to the remaining carbon (C-25) of the side chain indicated the presence of a hydroxyl group at C-25. These data revealed the structure of the side chain with a hydroxyl group at C-25 and a double bond at C-23 and C-24, which was supported by the chemical shift in comparison with those of related hydroxylated ginsenosides [10]. Thus, based on the above data, the structure of compound B was assigned as 3-O-[β-D-glucopyranosyl(1→2)-β-D-glucopyranosyl]-3β,12β,20(S), 25-tetrahydroxydammar-23-ene.

In another embodiment of the instant invention, compound E was synthesized from 20(R)-Rg$_3$ by using epoxidation dibetal catalyst solution, which oxidized 24,25-double bond into 24,25-epoxide. However, the resulting 24,25-epoxy compounds are quite unstable in the existence of the 20-hydroxy group and are immediately changed into 20,24-epoxides [11]. The formation of 20,24-epoxides in compound E was evidenced by the large down-field shift of C-20 (Δδ$_C$=13.3) and C-23 (Δδ$_C$=5.3), as well as the displacement of olefinic carbon signals with oxygenated carbon signals [δ$_C$ 87.4, 86.2 (C-24), δ$_C$ 70.9, 70.5 (C-25)] in comparison with that of 20(R)-type ginsenosides [12], and was further supported by comparing the chemical shifts to that of 20(S)-epoxides [13]. Compound E was found to be an equivalent mixture of 24(R) and 24(S)-epimer based on the fact that the signals of C-17, 20 to 27 appeared in pairs in the $^{13}$C-NMR spectrum (as shown in Table 2). On the basis of above data, the structure of compound E was assigned as 3-O-[β-D-glucopyranosyl(1→2)-β-D-gluco-pyranosyl]-20(R),24 (S)-epoxydammarane-3β,12β-triol and its 24(R) epimer.

TABLE 2

$^{13}$C-NMR data of the chemically synthesized new metabolites (in pyridine-d$_5$)

| C | A$^a$ | B$^b$ | C$^a$ | D$^b$ | E |
|---|---|---|---|---|---|
| 1 | 39.4 | 39.3 | 39.4 | 39.6 | 39.5 |
| 2 | 27.7 | 26.9 | 27 | 26.8 | 28.4 |
| 3 | 89.2 | 89 | 89.2 | 89.2 | 89.2 |
| 4 | 40 | 39.8 | 40 | 40.1 | 40 |
| 5 | 56.6 | 56.5 | 56.6 | 56.7 | 56.6 |
| 6 | 18.4 | 18.6 | 18.6 | 18.9 | 18.7 |
| 7 | 35.4 | 35.3 | 35.4 | 35.6 | 35.5 |
| 8 | 40.3 | 40.1 | 40.3 | 40.4 | 40.3 |
| 9 | 50.3 | 50.5 | 50.6 | 50.6 | 50.5 |
| 10 | 37.2 | 37 | 37.2 | 37.5 | 37.2 |
| 11 | 30.2 | 32.2 | 31.6 | 32.5 | 31.4 |
| 12 | 71.3 | 71.1 | 71.2 | 70.2 | 71 |
| 13 | 48.8 | 49 | 49.5 | 49.8 | 49.9 |
| 14 | 52 | 51.8 | 52 | 51.2 | 52 |
| 15 | 30.2 | 31.4 | 30.1 | 31.8 | 51.8 |
| 16 | 27 | 26.8 | 26.9 | 26.8 | 26.2 |
| 17 | 55.1 (54.9) | 54.2 | 51 | 52.3 | 51.2 (51.1) |
| 18 | 16.8 | 16.6 | 16.9 | 16.3 | 16.9 |
| 19 | 16.6 | 16 | 16.7 | 16 | 16 |
| 20 | 73.4 (73.3) | 73.4 | 73.3 | 74.2 | 86.5 (86.4) |
| 21 | 27.2 | 27.7 | 23.2 | 23 | 21.6 (19.3) |
| 22 | 31.6 | 39.8 | 39.6 | 46.6 | 39.4 (38.4) |
| 23 | 30.9 | 123.3 | 32.4 | 121.5 | 27.7 (27.3) |
| 24 | 76.6 (76.3) | 141.8 | 76.3 (76.4) | 142.6 | 87.4 (86.2) |
| 25 | 150.5 | 69.9 | 150.5 | 70.2 | 70.9 (70.5) |
| 26 | 110.4 (110.1) | 30.8 | 110.6 (110.4) | 31.2 | 26.4 (26.8) |
| 27 | 18.7 | 30.8 | 18.4 | 31.2 | 30.3 (27.0) |
| 28 | 28.4 | 28.3 | 28.4 | 28.6 | 31.7 |
| 29 | 16.1 | 17.1 | 16.1 | 16.8 | 16.7 |
| 30 | 17.3 | 16.7 | 17.6 | 17.6 | 17.4 |
| 1' | 105.4 | 105.1 | 105.4 | 105.4 | 105.4 |
| 2' | 83.6 | 83.3 | 83.7 | 83.7 | 83.6 |
| 3' | 78.2 | 78 | 78.6 | 78.5 | 78.4 |
| 4' | 71.9 | 71.7 | 71.9 | 71.8 | 71.8 |
| 5' | 78.4 | 78.3 | 78.4 | 78.6 | 78.3 |
| 6' | 62.8 | 62.9 | 63 | 63.2 | 63.1 |
| 1" | 106.3 | 106 | 106.3 | 106.3 | 106.3 |
| 2" | 77.4 | 77.1 | 77.5 | 77.4 | 77.4 |
| 3" | 78.6 | 78.4 | 78.6 | 78.7 | 78.6 |
| 4" | 71.9 | 71.7 | 71.9 | 71.2 | 71.9 |
| 5" | 78.6 | 78.1 | 78.2 | 78.3 | 78.6 |
| 6" | 62.1 | 62.7 | 63.1 | 63.1 | 63 |

$^a$150 MHz for $^{13}$C-NMR; $^b$75 MHz for $^{13}$C-NMR; The signals were assigned by comparing with those of reference compounds reported previously [7, 10, 13-14].

4. Conclusion

The methods of synthesizing novel ginsenoside derivative compounds A-G and the chemical structures thereof are described therein.

EXAMPLE 2

This example described the use of compounds A-G in the protection against ischemia/reperfusion injury in heart.

1. Cell Line and Reagents

Embryonic rat heart derived cell line H9c2 (2-1), shorted in H9c2 cells, was purchased from ATCC (CRL-1446), which is a permanent cell line and derived from embryonic BDIX rat ventricular heart tissue. Dulbecco's Modified Eagle Medium, Fetal Bovine Serum, and Penicillin-Streptomycin-Glutamine, 2.5% Trypsin/EDTA solution, Phosphate-buffered saline from GIBCO® (Invitrogen™) were used.

2. Cell Culture Methods

H9c2 cells were cultured in DMEM medium supplemented with 10% fetal bovine serum, 1% glutamine, 50 U/ml penicillin and 50 mg/ml streptomycin. The culture atmosphere for H9c2 cells was 95% air with 5% carbon dioxide ($CO_2$) at 37.0° C. The medium was replaced every 2-3 days. A stock of cells was grown in a 100 $cm^2$ culture dish and split before confluence at a subcultivation ratio of 1:4. Cells used for experiments were seeded at a density of $1.0 \times 10^4$ cells/well in a 96-well culture plate, and cells in each well were allowed to grow to 60-80% confluence within 24 h prior to drug treatment.

3. Hypoxia/Reoxygenation (H/R) Protocols

After treatment with desired concentrations of drug for 3 h, the cells were washed twice with Krebs-Ringer Bicarbonate buffer (KRB; 115 mM NaCl, 4.7 mM KCl, 2.5 mM CaCl2, 1.2 mM KH2PO4, 1.2 mM MgSO4, 24 mM NaHCO3, 10 mM HEPES; pH 7.4). Aliquots of KRB supplemented with 0.01% (w/v) BSA were added to the cells immediately prior to hypoxia. A Billups-Rothenberg modular incubator chamber (Billups-Rothenberg, Inc.; DelMar, Calif.) was used to produce an in vitro Hypoxia/Reoxygenation challenge. In essence, cells were placed in the sealed chamber and the chamber was flushed with 100% nitrogen for 5 min at a flow rate of 25 liter/min. After closing all sealable connectors, the chamber was transferred to an incubator and the cells in the chamber were subjected to a period of hypoxia at 37° C. Reoxygenation was initiated by opening the chamber and then replacing the KRB with fresh DMEM medium. The cells were then cultured in the incubator under an atmosphere of 5% (v/v) CO2 in air at 37° C. for designed periods.

4. Cell Viability Assay

The cell viability was measured using the MTT colorimetric assay, which was based on the conversion of MTT to formazan crystals by mitochondrial dehydrogenase. Briefly, H9c2 cells were seeded in 96-well plates at $1 \times 10^4$ cells/well and incubated at 37° C. for 48 h. The cells were then treated with DMSO (H/R control), diazoxide (50 μM). Compounds A-G (at two concentrations of 12.5 μM or 25 μM) and incubated under hypoxia condition. The cells without any treatment and incubated under normoxia condition were used as normal control. At the end of the treatments, 10 ml MTT (5 mg/ml) was added for 4 h and then 100 ml MTT buffer (10% SDS solution, pH7.4) was added to each well. After overnight incubation and 30 s vibration, the absorbance was read at 490 nm wavelength. Results were expressed as the ratio of the number of viable cells with treatments relative to that of the normoxia control.

5. Statistical Analysis

Data were expressed as mean±SEM. One-way ANOVA with multiple comparisons using the Dunnett's Multiple Comparison Test was used to analyze differences between groups. All statistical analysis was performed using Prism 5 for Windows version 5.00 (GraphPad software, Inc., La Jolla, Calif. 92037 USA). Differences were considered significant if $p<0.05$.

6. Results

Figure 2:
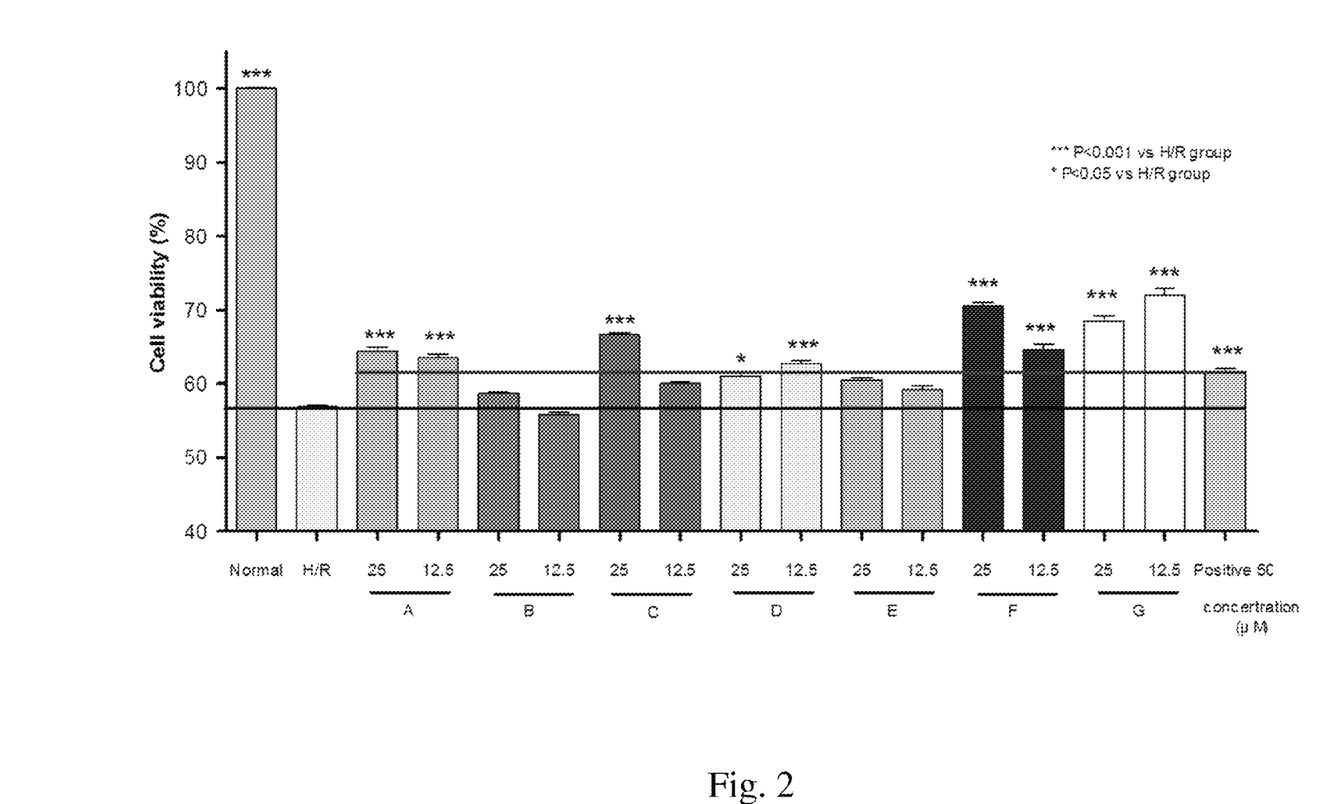
FIG. 2 shows the in vitro bioassay result of protective effect of gensenoside derivative compounds A-G in I/R injury in heart according to one embodiment of the present invention, in which the injury was induced by hypoxia/reoxygenation in H9c2 cells.

As shown in FIG. 2, the viability in cardiomyocyte cells of the H/R control group (H/R) decreased to approximately 50% to 56.83±0.24%, while that of the positive control group (Positive 50) increased to 61.69±0.37% ($p<0.001$). The protective effect of derivative compounds A-G in ischemia/reperfusion injury in heart was evaluated on hypoxia/oxygenation-induced toxicity cardiomyocyte cell model. As shown in FIG. 2, all derivative compounds (A-G) caused viabilities to cells underwent I/R at concentrations (12.5 or 25 μM) and also exhibited significant protective effects as compared with the H/R control group. The protective effects of derivative compounds A, C, D, F and G were all higher than the positive control drug. The order of cardioprotective effects of these 7 derivative compounds was as follows: G>F>C>A>D>B, E. The highest protective effect was observed in derivative compound G at the concentration of 25 μM (70.60±0.44%), while the lowest effective effect was observed in derivative compound D at the concentration of 25 μM (61.06±0.30%).

7. Conclusion

In vitro studies suggested that all derivative compounds (A-G and $Rg_3$) have protective effect in cardiomyocyte H9c2 cells against ischemia/reperfusion injury induced by hypoxia/reoxygenation.

EXAMPLE 3

Figure 3:
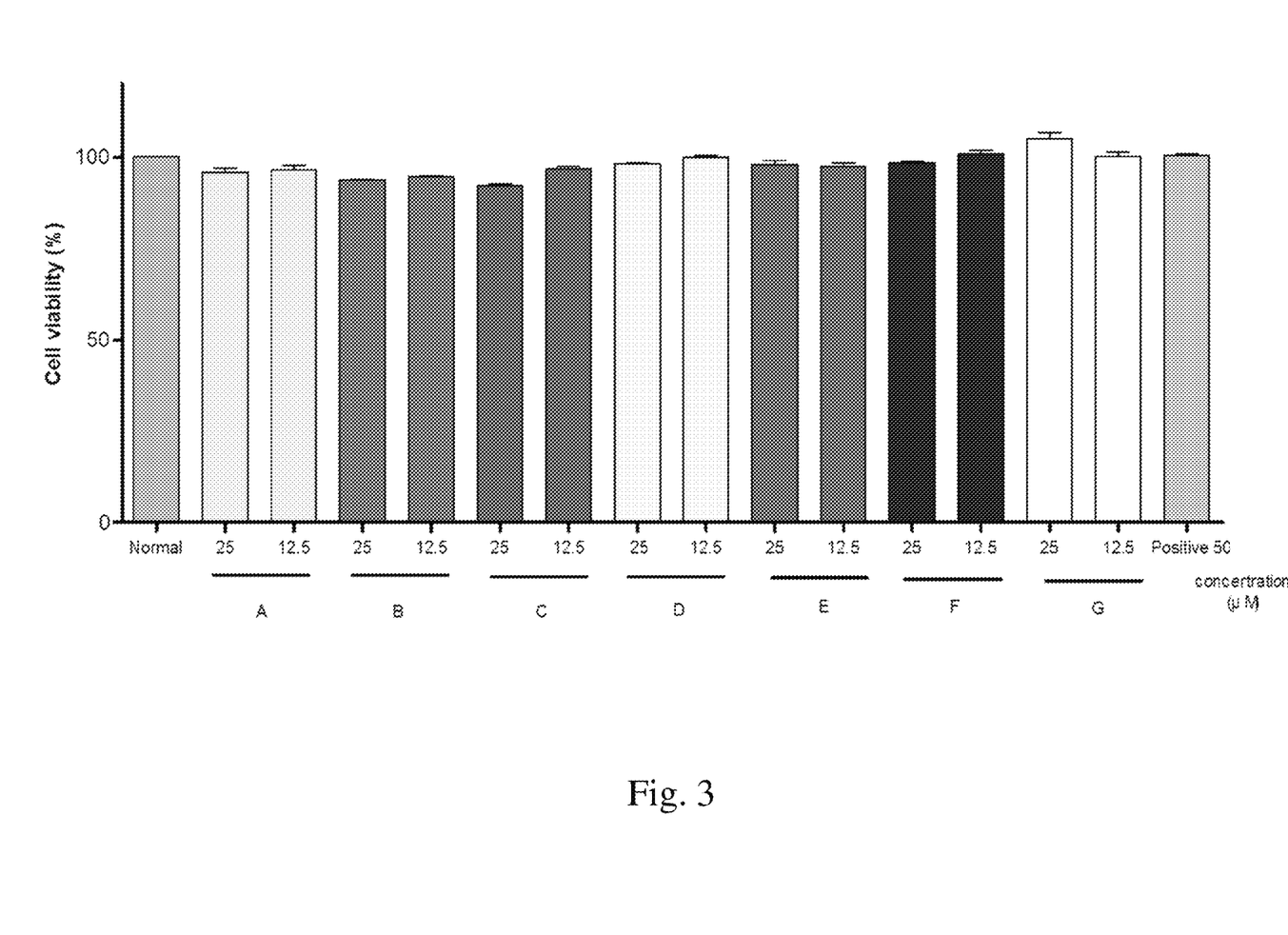
FIG. 3 shows the result of a cytotoxicity study of ginsenoside derivative compounds in H9c2 cells in normaxia condition according to one embodiment of the present invention.

This example described the cytotoxic effect study of compounds A-G in H9c2 cells in normoxia condition at the equivalent dosage with results as shown in FIG. 3.

1. Cell Line and Reagents, Cell Culture Methods, Cell Viability Assay and Statistical Analysis The cell line and reagents used, and cell culture methods, cell viability assay and statistical analysis employed were described in Example 2.

2. Normoxia Protocols

The cells were treated with desired concentrations of compounds A-G for 3 h, then the medium thereof was replaced with DMEM medium with 10% fetal bovine serum, 1% glutamine, 50 U/ml penicillin and 50 mg/ml streptomycin. The culture atmosphere for normaxia condition was 95% air with 5% carbon dioxide (CO2) at 37.0° C. The cells were then cultured in the incubator for designed periods. The cells without any treatment and incubated under normoxia condition were used as positive control.

3. Results

Results were expressed as the ratio of the number of viable cells with treatments relative to that of the positive control. As shown in FIG. 3, cytotoxic effects of derivative compounds A-G at the equivalent dosages were evaluated under normoxia condition. As compared with positive control group (Positive 50), compound A at 12.5 and 25 μM, as well as compound B at 12.5 and 25 μM showed no statistically significant cytotoxicity.

4. Conclusion

Compounds A, B, C, D, E, F, G have no significant cytotoxicity in H9c2 cells at equivalent dosages in normoxia condition.

In summary, the results of Examples 1-3 demonstrate that the compounds of the present invention have protective effect in cardiomyocyte H9c2 cells against ischemia/reperfusion injury induced by hypoxia/reoxygenation, but no significant cytotoxicity at equivalent dosages in normoxia condition.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

References

1. Hobbs, A.; Foster, P.; Prescott, C.; Scotland, R.; Ahluwalia, A., Natriuretic peptide receptor-C regulates coronary blood flow and prevents myocardial ischemia/reperfusion

1. Zhou, H.; Hou, S. Z.; Luo, P.; Zeng, B.; Wang, J. R.; Wong, Y. F.; Jiang, Z. H.; Liu, L., Ginseng protects rodent hearts from acute myocardial ischemia-reperfusion injury through GR/ER-activated RISK pathway in an endothelial NOS-dependent mechanism. J Ethnopharmacol 2011, 135 (2), 287-98.
3. Scott, G. I.; Colligan, P. B.; Ren, B. H.; Ren, J., Ginsenosides Rb1 and Re decrease cardiac contraction in adult rat ventricular myocytes: role of nitric oxide. Br J Pharmacol 2001, 134 (6), 1159-65.
4. Kang, S. Y.; Schini-Kerth, V. B.; Kim, N. D., Ginsenosides of the protopanaxatriol group cause endothelium-dependent relaxation in the rat aorta. Life Sci 1995, 56 (19), 1577-86.
5. Yi, X. Q.; Li, T.; Wang, J. R.; Wong, V. K.; Luo, P.; Wong, I. Y.; Jiang, Z. H.; Liu, L.; Zhou, H., Total ginsenosides increase coronary perfusion flow in isolated rat hearts through activation of PI3K/Akt-eNOS signaling. Phytomedicine 2010, 17 (13), 1006-15.
6. Wang, J. R.; Zhou, H.; Yi, X. Q.; Jiang, Z. H.; Liu, L., Total ginsenosides of Radix Ginseng modulates tricarboxylic acid cycle protein expression to enhance cardiac energy metabolism in ischemic rat heart tissues. Molecules 2012, 17 (11), 12746-57.
7. Jiang, Z.-H.; Fukuoka, R.; Aoki, F.; Tanaka, T.; Kouno, I., Dammarane-type triterpene glycosides from the leaves of Rhoiptelea chiliantha. Chem. Pharm. Bull. 1999, 47 (Copyright (C) 2012 American Chemical Society (ACS). All Rights Reserved.), 257-262.
8. Tu, Y.; Wang, Z.-X.; Shi, Y., An Efficient Asymmetric Epoxidation Method for trans-Olefins Mediated by a Fructose-Derived Ketone. J. Am. Chem. Soc. 1996, 118 (Copyright (C) 2012 American Chemical Society (ACS). All Rights Reserved.), 9806-9807.
9. (a) Ko, S. R.; Suzuki, Y.; Kim, Y. H.; Choi, K. J., Enzymatic synthesis of two ginsenoside Re-beta-xylosides. Biosci Biotechnol Biochem 2001, 65 (5), 1223-6; (b) Ko, S. R.; Choi, K. J.; Suzuki, K.; Suzuki, Y., Enzymatic preparation of ginsenosides Rg2, Rh1, and F1. Chem Pharm Bull (Tokyo) 2003, 51 (4), 404-8.
10. Yoshikawa, M.; Murakami, T.; Ueno, T.; Hirokawa, N.; Yashiro, K.; Murakami, N.; Yamahara, J.; Matsuda, H.; Saijoh, R.; Tanaka, O., Bioactive saponins and glycosides. IX. Notoginseng (2): structures of five new dammarane-type triterpene oligoglycosides, notoginsenosides-E, -G, -H, -I, and -J, and a novel acetylenic fatty acid glycoside, notoginsenic acid β-sophoroside, from the dried root of Panax notoginseng (Burk.) F. H. Chen. Chem. Pharm. Bull. 1997, 45 (Copyright (C) 2012 American Chemical Society (ACS). All Rights Reserved.), 1056-1062.
11. Kasai, R.; Hara, K.; Dokan, R.; Suzuki, N.; Mizutare, T.; Yoshihara, S.; Yamasaki, K., Major metabolites of ginseng sapogenins formed by rat liver microsomes. Chem Pharm Bull (Tokyo) 2000, 48 (8), 1226-7.
12. Odani, T.; Tanizawa, H.; Takino, Y., Studies on the absorption, distribution, excretion and metabolism of ginseng saponins IV. Decomposition of ginsenoside-Rg1 and -Rb1 in the digestive tract of rats. Chem Pharm Bull (Tokyo) 1983, 31 (10), 3691-7.
13. Duc, N. M.; Kasai, R.; Ohtani, K.; Ito, A.; Nham, N. T.; Yamasaki, K.; Tanaka, O., Saponins from Vietnamese ginseng, Panax vietnamensis Ha et Grushv. collected in central Vietnam. III. Chem Pharm Bull (Tokyo) 1994, 42 (3), 634-40.
14. (a) Yoshikawa, M.; Murakami, T.; Ueno, T.; Yashiro, K.; Hirokawa, N.; Murakami, N.; Yamahara, J.; Matsuda, H.; Saijoh, R.; Tanaka, O., Bioactive saponins and glycosides. VIII. Notoginseng (1): new dammarane-type triterpene oligoglycosides, notoginsenosides-A, B, -C, and -D, from the dried root of Panax notoginseng (Burk.) F. H. Chen. Chem Pharm Bull (Tokyo) 1997, 45 (6), 1039-45; (b) Nguyen, M. D.; Kasai, R.; Ohtani, K.; Ito, A.; Nguyen, T. N.; Yamasaki, K.; Tanaka, O., Saponins from Vietnamese Ginseng, Panax vietnamensis HA et Grushv. Collected in central Vietnam. II. Chem Pharm Bull (Tokyo) 1994, 42 (1), 115-22.

What is claimed is:

1. A method of treating ischemia/reperfusion injury in cardiomyocytes comprising administering an effective amount of a ginsenoside derivative compound to a subject in need thereof, wherein said compound is represented by formula (V) or any optical isomer thereof, or formula (VI) or any optical isomer thereof 2. The method according to claim 1, wherein said ginsenoside derivative is selected from a group consisting of
3-O-[β-D-glucopyranosyl(1→2)-β-D-glucopyranosyl]-3β,12β,20(S),24(S)-tetrahydroxydammar-25-ene and 24(R) epimer thereof;
3-O-[β-D-glucopyranosyl(1→2)-β-D-glucopyranosyl]-3β,12β,20(S),25-tetra-hydroxydammar-23-ene;
3-O-[β-D-glucopyranosyl(1→2)-β-D-glucopyranosyl]-3β,12β,20(R),24(S)-tetrahydroxydammar-25-ene and 24(R) epimer thereof; and
3-O-[β-D-glucopyranosyl(1→2)-β-D-glucopyranosyl]-3β,12β,20(R),25-tetrahydroxydammar-23-ene.

* * * * *